US00PP24744P3

(12) United States Plant Patent
Bradford

(10) Patent No.: US PP24,744 P3
(45) Date of Patent: Aug. 12, 2014

(54) CHERRY TREE NAMED 'GLENEARLY'

(50) Latin Name: *Prunus avium*
Varietal Denomination: Glenearly

(71) Applicant: Lowell Glen Bradford, Le Grand, CA (US)

(72) Inventor: Lowell Glen Bradford, Le Grand, CA (US)

( * ) Notice: Subject to any disclaimer, the term of this patent is extended or adjusted under 35 U.S.C. 154(b) by 88 days.

(21) Appl. No.: 13/694,607

(22) Filed: Dec. 13, 2012

(65) Prior Publication Data

US 2014/0173788 P1 Jun. 19, 2014

(51) Int. Cl.
*A01H 5/00* (2006.01)

(52) U.S. Cl.
USPC ..... Plt./181

(58) Field of Classification Search
USPC ..... Plt./181
See application file for complete search history.

(56) References Cited

U.S. PATENT DOCUMENTS

PP12,859 P2 8/2002 Bradford

*Primary Examiner* — Annette Para

(57) ABSTRACT

The present invention relates to a cherry tree, *Prunus avium*, and more particularly to a new and distinct variety broadly characterized by a medium size, moderately vigorous, hardy, self unfruitful, productive and regular bearing tree. The fruit matures under the ecological conditions described in the early part of May, with first picking on May 7, 2012. The fruit is uniformly medium in size, sweet in flavor, somewhat oblate in shape, clingstone in type, firm in texture, dark red in flesh color, and very dark red in skin color.

1 Drawing Sheet

Botanical classification: *Prunus avium.*
Varietal denomination: 'GLENEARLY'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits, usually to capture recessive traits. The present invention relates to a new and distinct variety of cherry tree, which has been denominated varietally as 'Glenearly'.

During the blooming season of 2002 I hybridized a tree of 'Brooks' (unpatented) cherry as the selected seed parent by 'Glenred' (U.S. Plant Pat. No. 12,859) cherry as the selected pollen parent. The fruit of this cross was gathered in the spring of 2002, and the seeds were removed from the fruit, germinated, and grown as seedlings on their own root in my greenhouse. Upon reaching dormancy that year the seedlings were transplanted as a group to a cultivated area of my experimental orchard located near Le Grand, Calif., in Merced County (San Joaquin Valley). During the fruit evaluation season of 2006 I selected the present variety as a single tree from the group described above. Subsequent to origination of the present variety of cherry tree, I asexually reproduced it by budding and grafting in the experimental orchard described above, and such reproduction of plant and fruit characteristics were true to the original plant in all respects. The reproduction of the variety included the use of 'Colt' (unpatented) rootstock, upon which the present variety was compatible and true to type.

The present variety is similar to its seed parent, 'Brooks' (unpatented) cherry, by being moderately vigorous, by being self unfruitful but moderately productive, by having reniform glands, and by producing commercial cherries for long distant shipping, but is distinguished therefrom by blooming about seven days earlier and by producing cherries that are darker red in skin color, that are much darker red in flesh color, that are much less susceptible to skin cracking, and that mature about five days earlier.

The present variety is most similar its pollen parent, 'Glenred' (U.S. Plant Pat. No. 12,859) cherry, by being self unfruitful, by having reniform glands, and by producing fruit that is dark red in skin color, dark red in flesh color, firm, sweet, and fairly crack resistant, but is distinguished therefrom by blooming about three days earlier, by being somewhat less susceptible to over-production, and by producing cherries that are slightly smaller, that are clingstone instead of semi-freestone, and that ripen about five days earlier.

SUMMARY OF VARIETY

In summary, the present variety is characterized by a medium size, moderately vigorous, hardy, self unfruitful, productive and regular bearing tree. The fruit matures under the ecological conditions described in the early part of May, with first picking on May 7, 2012. The fruit is uniformly medium in size, sweet in flavor, somewhat oblate in shape, clingstone in type, firm in texture, dark red in flesh color, and very dark red in skin color.

DRAWING

The accompanying photograph displays four fruits with the stems attached, two whole fruits detached from the stems to exhibit the skin color and form, two fruits sectioned to reveal the flesh and fibers, an individual stone, two insets depicting flowers and buds, a typical tip shoot, and several leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., and was developed at the state of full ripe on May 15, 2012, on the original tree during its tenth growing season. All major color code designations are by reference to the Inter-Society Color Council, National Bureau of Standards. Common color names are also used occasionally.

PARENTAGE

Seed parent: 'Brooks' cherry (unpatented).
Pollen parent: 'Glenred' cherry (U.S. Plant Pat. No. 12,859).

TREE

Size: Medium, maintained to a height of 12' [3.66 m.] and a spread of 6' [1.83 m.] after ten growing seasons utilizing typical pruning.
Vigor: Medium vigor, responding typically to irrigation and fertilization. The plant should be grown on a standard commercial rootstock for production purposes.
Growth: Upright and open.
Form: Central leader.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive.
Fertility: Self-sterile, must be cross pollinated by another early blooming cherry variety, such as 'Glenare' (U.S. Plant Pat. No. 15,180) or 'Glenoia' (U.S. Plant Pat. No. 15,157).
Bearing: Regular bearer, with no crop failures observed.
Trunk:
- *Size.*—Medium, reaching a maximum diameter of 3¾" [95.3 mm.] after the tenth growing season.
- *Texture.*—Medium shaggy.
- *Bark color.*—A Grayish brown [61. gy.Br] and Moderate brown [58. m.Br] variegation with Strong brown [55. s.Br] crevices present.
- *Lenticels.*—Approximate Number Per Square Inch: 8. Color: Strong brown [55. s.Br]. Average Size: ¼" [6.4 mm.] to ⅝" [15.9 mm.]. Shape: Elongated, eye-shaped.

Branches:
- *Size.*—Diameter of central leader measured 12" above the first hanger is 2½" [63.5 mm.]. Diameter of first hanger is 1¼" [31.8 mm.].
- *Texture.*—Smooth on first and second year wood, increasing roughness with age.
- *Color.*—1st Year Wood topside: Grayish red [19. gy.R]. 1st Year Wood underside: Brilliant yellow green [116. brill.YG]. 2nd Year Wood: Grayish brown [61. gy.Br] and Brownish gray [64. brGy] variegation.
- *Lenticels.*—Number Per Square Inch: About 18 on second year wood. Color: Brownish orange [54. brO]. Size: 1/64" [0.4 mm.] to 1/16" [1.6 mm.]. Shape: Eye-shaped, elongated.

Leaves:
- *Size.*—Medium. Average Length: 6⅛" [155.6 mm.]. Average Width: 2" [50.8 mm.].
- *Arrangement.*—Alternate.
- *Thickness.*—Medium.
- *Form.*—Elliptical.
- *Apex.*—Acuminate.
- *Base.*—Rounded.
- *Surface.*—Smooth.
- *Color.*—Dorsal Surface: Moderate olive green [125. m.OlG]. Ventral Surface: Deep yellow green [118. deep YG].
- *Margin.*—Finely serrate.
- *Venation.*—Pinnately net veined.
- *Vein color.*—Brilliant yellow green [116. brill.YG].
- *Petiole.*—Average Length: 1" [25.4 mm.]. Average Thickness: ⅛" [3.2 mm.]. Color: Grayish red [19. Gy.R] on the topside and Moderate yellow green [120. m.YG] underneath.
- *Stipules.*—Number: 2 to 6 per leaf at development stage. Average Length: ¼" [6.4 mm.]. Color: Moderate yellow green [120. m.YG] becoming Moderate olive green [125. m.OlG] with age.
- *Glands.*—Number: Mostly 2 per leaf. Position: Oppositely positioned on the petiole just below the leaf blade. Size: Medium. Form: Reniform to oval. Color: Strong yellow green [117. s.YG] becoming Dark olive green [126. d.OlG] with age.
- *Leaf buds.*—Pointed, medium.

Flower buds:
- *Hardiness.*—Hardy, with respect to central California winters.
- *Diameter.*—Typically 5/16" [7.9 mm.] 3 days before bloom.
- *Length.*—Typically ⅝" [15.9 mm.] 3 days before bloom.
- *Form.*—Free.
- *Surface.*—Non-pubescent.
- *Tip color.*—White [263. white].

Flowers: Perfect, complete, perigynous, usually a single pistil, typically about twenty stamens, five sepals and petal locations alternately positioned.
- *Average flower diameter.*—1¼" [31.8 mm.].
- *Number of petals.*—Usually five, very few have extra petals or fragments.
- *Petal shape.*—Circular to slightly oval.
- *Petal margin.*—Moderately wavy with occasional serrations.
- *Average petal diameter.*—9/16" [14.3 mm.].
- *Average petal length.*—11/16" [17.5 mm.].
- *Petal apex.*—Rounded with a small notch on most.
- *Petal base.*—Cuneate.
- *Petal color.*—White [263. white].
- *Anther color.*—Light yellow [86. l.Y].
- *Stigma color.*—Light greenish yellow (101. l.gY).
- *Sepal color.*—Strong reddish brown [40. s.rBr] over Strong yellow green [117. s.YG].
- *Sepal length.*—¼" [6.4 mm.].
- *Sepal width.*—3/16" [4.8 mm.].
- *Average pistil length.*—9/16" [14.3 mm.].
- *Average stamen length.*—½" [12.7 mm.].

*Fragrance.*—Moderate.
*Pollen production.*—Moderate.
*Bloom density.*—Heavy.
*Blooming period.*—Early, three days before 'Glenred' (U.S. Plant Pat. No. 12,859).
*Onset of bloom.*—One percent on Mar. 9, 2012.
*Date of full bloom.*—Mar. 16, 2012.
*Duration of bloom.*—One to two weeks, dependent on ambient temperature.
*Number per cluster.*—Usually 2 to 10, 6 average.

FRUIT

Maturity when described: Full ripe, May 15, 2012.
Date of first picking: May 7, 2012.
Date of last picking: May 15, 2012.
Size: Uniform, medium.
*Average diameter axially.*—7/8" [22.2 mm.].
*Average diameter across cheek plane.*—15/16" [23.8 mm.].
*Average diameter across suture plane.*—1 1/8" [28.6 mm.].
*Typical seight.*—0.32 ounces [9 grams].
Form: Uniform, symmetrical, somewhat oblate.
*Cheek plane form.*—Oblate.
*Suture plane form.*—Oval.
*Axial view form.*—Elliptical.
Suture: A Blackish red [21. Blackish R] line located in a shallow trough extending almost entirely around the fruit.
Ventral surface: Rounded, lipped toward the apex on both sides.
Lips: Equal.
Cavity: Flaring, rounded, suture showing on one side.
*Depth.*—1/8" [3.2 mm.].
*Breadth.*—3/8" [9.5 mm.].
Base: Slightly truncate if viewed in the suture plane, cordate if viewed parallel to the suture.
Apex: Rounded to slightly cordate.
Pistil point: An inconspicuous dot.
Stem: Medium.
*Average length.*—1 3/8" [34.9 mm.].
*Average width.*—1/16" [1.6 mm.].
Skin:
*Thickness.*—Medium.
*Surface.*—Smooth.
*Tenacity.*—Tenacious to the flesh.
*Astringency.*—Very slight.
*Tendency to crack.*—Rarely observed in dry seasons, fairly resistant to cracking in wet season.
*Color.*—A Very dark purplish red [260. v.d.pR] over a Dark red [16. d.R] background.
Flesh:
*Color.*—Deep red [13. deep R] near the skin and Dark red [16. d.R] near the stone.
*Surface of pit cavity.*—Covered with Very deep red [14. v.deep R] broken fibers when twisted away from the stone.
*Amygdalin.*—Moderate.
*Juice.*—Abundant, rich.
*Juice color.*—Dark red [16. d.R].
*Texture.*—Firm, crisp, melting.
*Fibers.*—Abundant, fine, tender.
*Ripens.*—Mostly even, slightly earlier at the apex.
*Flavor.*—A nice balance of acid and sugar, typically 20-24 brix.
*Aroma.*—Very slight.
*Eating quality.*—Very good.

STONE

Type: Clingstone.
Form: Oval.
Hilum: Narrow, oblong.
Base: Straight.
Apex: Rounded.
Sides: Equal.
Surface: Fairly smooth.
External color of stone: Light yellowish brown [76. l.yBr] when first removed.
Pit wall color when cracked: Pale orange yellow [73. p.OY].
Cavity surface color: Pale orange yellow [73. p.OY].
Average pit wall thickness: 1/16" [1.6 mm.].
Average width: 3/8" [9.5 mm.].
Average length: 3/8" [9.5 mm.].
Average breadth: 5/16" [7.9 mm.].
Tendency to split: None observed in dry season.
Kernel:
*Form.*—Oval.
*Skin color.*—Pale yellow [89. p.Y] when first removed.
*Pellicle color.*—Grayish yellow [90. gy.Y].
*Vein color.*—Moderate yellow [87. m.Y].
*Taste.*—Bitter.
*Viable.*—Yes.
*Average width.*—3/16" [4.8 mm.].
*Average length.*—5/16" [7.9 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of cherry tree, substantially as illustrated and described, that is most similar to the 'Glenred' (U.S. Plant Pat. No. 12,859) cherry by having reniform glands, and by producing fruit that is dark red in skin color, dark red in flesh color, firm, sweet, and fairly crack resistant, but is distinguished therefrom by blooming about three days earlier, by being somewhat less susceptible to over-production, and by producing cherries that are slightly smaller, that are clingstone instead of semi-freestone, and that ripen about five days earlier.

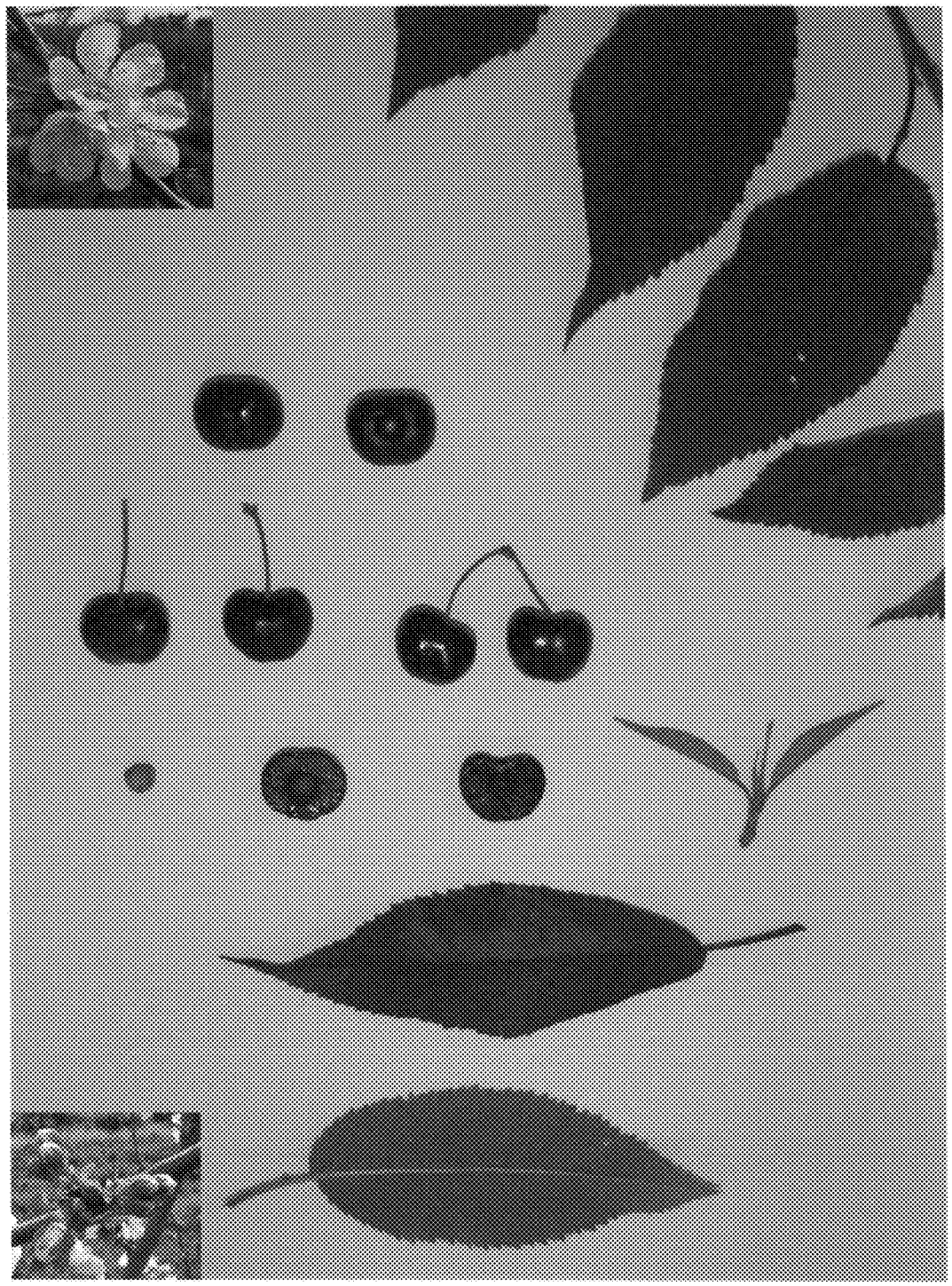

* * * * *